(12) United States Patent
Berekaa

(10) Patent No.: US 12,012,625 B2
(45) Date of Patent: Jun. 18, 2024

(54) METHOD FOR PRODUCING BIOACTIVE COMPOSITION

(71) Applicant: Imam Abdulrahman Bin Faisal University, Dammam (SA)

(72) Inventor: Mahmoud Mohamed Berekaa, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 8 days.

(21) Appl. No.: 16/951,331

(22) Filed: Nov. 18, 2020

(65) Prior Publication Data

US 2022/0154225 A1    May 19, 2022

(51) Int. Cl.
*C12P 1/04*    (2006.01)
*A01N 63/22*   (2020.01)

(52) U.S. Cl.
CPC ............... *C12P 1/04* (2013.01); *A01N 63/22* (2020.01)

(58) Field of Classification Search
CPC .................................. C12P 1/04; A01N 63/22
See application file for complete search history.

(56) References Cited

U.S. PATENT DOCUMENTS

| | | | |
|---|---|---|---|
| 9,493,792 B1 | 11/2016 | Kiran et al. | |
| 2015/0045288 A1 | 2/2015 | Mygind et al. | |
| 2018/0066291 A1* | 3/2018 | Berekaa ................ | C12P 7/625 |

FOREIGN PATENT DOCUMENTS

| | | |
|---|---|---|
| CN | 102977082 A | 3/2013 |
| WO | WO 2006/069610 A2 | 7/2006 |
| WO | WO 2006/117019 A1 | 11/2006 |
| WO | WO 2017/093977 A1 | 6/2017 |

OTHER PUBLICATIONS

Johnson et al., "Evaluation of 16S rRNA gene sequencing for species and strain-level microbiome analysis", Nature Communications vol. 10, Article No. 5029 (2019) (Year: 2019).*
Ram et al., "Optimization and Charecterization Ofintracellular Orange Fluorescentpigment From Bacillus Endophyticus (AVP-9(Kf527823)", Int J Curr Pharm Res, vol. 9, Issue 5, 67-74, 2017 (Year: 2017).*
Mantri Sai Ram, et al., "Optimization and Charecterization of Intracellular Orange Fluorescent Pigment from Bacillus Endophyticus (AVP-9(Kf527823)", International Journal of Current Pharmaceutical Research, vol. 9, Issue 5, 2017, pp. 67-74.
Nokku Pradeep Kumar, et al., "Fluorescent Bacillus endophyticus AVP9-Multiple potential for phosphate solubilization, plant growth promotion and bio control", International Journal of Scientific & Engineering Research, vol. 5, Issue 12, Dec. 2014, pp. 1401-1412.
Andrew Magyarosy, et al., "Chlorxanthomycin, a Fluorescent, Chlorinated, Pentacyclic Pyrene from a *Bacillus* sp.", Applied and Environmental Microbiology, vol. 68, No. 8, Aug. 2002, pp. 4095-4101.
Mobolaji A. Okulate, et al., "Antimicrobial activity of bioactive compound(s) produced by *Bacillus* species", Microbial Diversity Course, 2009, 14 pages.
Longzhan Gan, et al., "Biosynthesis, characterization and antimicrobial activity of silver nanoparticles by a halotolerant *Bacillus endophyticus* SCU-L", Preparative Biochemistry and Biotechnology, vol. 48, Issue 7, 2008, pp. 582-588 (Abstract only).
N.O. El-Helw, et al., "Characterization of natural bioactive compounds produced by isolated bacteria from compost of aromatic plants", Journal of Applied Microbiology, vol. 126, Issue 2, Aug. 24, 2018, pp. 443-451 (Abstract only).
Mahmoud Berekaa, et al., "Antibiotics Sensitivity and Heavy Metals Resistance in PHB-Producing Bacilli Isolated from Eastern Province, Saudi Arabia", International Journal of Agriculture & Biology, vol. 18, No. 6, 2016, pp. 1232-1236.
Taleb et al. ; The Antibacterial Activity of Date Syrup Polyphenols against *S. aureus* and *E. coli* ; frontiers in Microbiology ; vol. 7, Article 19 ; Feb. 26, 2016 ; 9 Pages.
Karkohota, et al., Brazilian J. Microbiol. (2022) 53:1395-1408.
Taleb, H., et al., The antimicrobial activity of date syrup polyphenols against *S. aureus* and *E. coli*. Front Microbiol. 2016, PMID: 26952177—9 pages.
Jia, et al. (2015; tos://doi.org/10.1371/journal.pone.0135104)—17 pages.
Lee, et al. (2012; https://www.ncbi.nlm.nih.gov/pmc/articles/PMC3458666/)—doi:10.1128/JB.01316-12, 2 pages.
Jia, et al. (2016; https://doi.org/10.1038/srep28794) 8 pages.
Lekota et al., "Whole genome sequencing and identification of *Bacillus endophyticus* and . . . ", BMC Microbiology, vol. 18 (2018)—15 pages.
Chauhan, et al. (2016; https://doi.org/10.1139/cjm-2016-0249).

(Continued)

*Primary Examiner* — Ruth A Davis
(74) *Attorney, Agent, or Firm* — Oblon, McClelland, Maier & Neustadt, L.L.P.

(57) ABSTRACT

A method for the preparation of bioactive compound by culturing a *Bacillus* species containing 16S rRNA having nucleotide sequence that is at least 80% identical to the nucleic acid sequence of the 16S rRNA of *B. endophyticus* DS43 of SEQ ID NO: 1. Tryptone soya broth (TSB) is an effective growth medium for the production of the bioactive compound. A growth medium used in the method contains date syrup and/or molasses. The isolated fluorescent bioactive compound has biocidal activity against bacteria including *Serratia marcescens, Staphylococcus aureus,* and *Escherichia coli.*

15 Claims, 5 Drawing Sheets
Specification includes a Sequence Listing.

(56) References Cited

OTHER PUBLICATIONS

Pang, et al. (2021; https://www.ncbi.nim.nih.gov/pmc/articles/PMC7920992/) ; doi: 10.3389/fmicb.2021.633141,—12 pages.
Reva, et al. (2002; https://pubmed.ncbi.nlm.nih.gov/11837291/); DOI: 1001039/00207713-52-1-101.
Leena, et al. (2018; https://www.aloki.hu/pdf/1602_12431256.pdf);http://dx.doi.org/10.15666/aeer/1602_12431256.

* cited by examiner

METHOD FOR PRODUCING BIOACTIVE COMPOSITION

REFERENCE TO A SEQUENCE LISTING

In accordance with 37 CFR § 1.52(e)(5), the present specification makes reference to a Sequence Listing submitted electronically as a .txt file named "520656US_ST25.txt" generated on Aug. 29, 2019 and is 1.08 kb in size. The entire content of the Sequence Listing is herein incorporated by reference.

BACKGROUND OF THE INVENTION

Field of the Invention

The invention falls within the fields of microbiology and biochemistry and involves culturing bacilli that produce a fluorescent material that exhibits antibacterial effects on *Serratia marcescens* and other pathogenic bacteria.

Description of Related Art

The "background" description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

Bioactive compounds with antimicrobial properties have attracted considerable interest recently as a result of the prevalence of infections caused by gram negative bacteria, which can be fatal. Also, the number of identified new strains of pathogenic and antibiotic resistant bacterial strains is increasing rapidly due to the wide use of antibiotics for treatment of farm animals and human diseases, particularly in hospitals and other health care facilities. Thus, there is an urgent need for identifying new and effective antimicrobial agents for treatment of patients infected with antibiotic-resistant bacteria.

*Serratia marcescens* is a gram negative, rod-shaped bacterium that occurs naturally in soil and water and produces red pigments at room temperature. It is often associated with urinary tract and respiratory infections, endocarditis, osteomyelitis, septicemia, wound infections, eye infections, and meningitis. Transmission this microorganism occurs by direct contact, for example, with a contaminated catheter or other medical device or supply. Colonies of *S. marcescens* have been observed growing on urinary track catheters and in supposedly sterile solutions. Contaminated intravenous pain control fluids were the cause of an outbreak of *S. marcescens* in a hospital in Taiwan [Chiang et al. Int. J. Infect. Dis. (2013) 17(9): e718-22. doi: 10.1016/j.ijid.2013.02.012—incorporated herein by reference in its entirety]. Most strains are resistant to several antibiotics.

Contamination of baby shampoo with *Serratia marcescens* caused multiple infections in a neonatal ICU in Saudi Arabia [Madani et al. J. Hosp. Infect (2011) 78(1): 16-19]. Other outbreaks of *S. marcescens* infection in neonatal units have been reported [Lima et al. (2011) Rev. Soc. Bras. Med. Trop. 44(1) Uberaba January/February 2011 hypertext transfer protocol:-//dx.doi.org/10.1590/S0037-86822011000100024]. Prefilled heparin and saline syringes infected with *S. marcescens* were the cause of bacteremia in a U.S. hospital [Chemaly et al. Amer J. Infect. Contr. (2011) 39(6) 521-524]. *S. marcescens* was isolated persistently from the grating and drains of eight central sinks in an Australian intensive care unit [Kotsanas Med. J. Aust. (2013) hypertext transfer protocol secure://doi.org/10.5694/mja12.11757—], and *S. marcescens* was found in the exit ports of oscillators in a Canadian pediatric intensive care unit (Macdonald et al. Ped. Crit. Care Med. (2011) 12 (6) p e282-e286 doi: 10.1097/PCC.0b013e31820ac42a]. Various attempts have been made to isolate antimicrobial compounds from microorganisms, but none disclose producing a fluorescent antimicrobial material effective against *S. marcescens*.

WO2017093977A1 discloses a method for the preparation of antimicrobial compound by fermenting aerobic endospore forming bacteria (AEFB), such as gram positive *Bacillus* spp WO 2017093977A1 describes cultivation of AEFB on liquid medium (LB, TSB/TSA or NB/NA) (in presence of TTC or tetrazolium salt as an inducing agent and under controlled temperature, pH and rpm) and using active cell-free supernatant (CFS) both in liquid and solid state for monoculture test. While this method involves culturing a bacterial strain in a medium containing an inducer and extracting the antimicrobial compound WO2006117019A1 discloses a composition comprising non-pathogenic sporulating bacteria for treating the udders of a lactating mammal. Several gram positive *Bacillus* species are disclosed including *Bacillus endophyticus*. WO2006069610A2 relates to a recombinant DNA based method for producing a biological agent, such as a chemical, by transforming a microorganism with exogenous DNA.

US20150045288A1 discloses cell free extracts, such as cell free supernatants from *Bacillus subtilis* that exhibit antibacterial activity against gram negative or gram positive bacteria. These cell free extracts contain bioactive compounds such as bacillibactin, polyketides, lipopeptide, anticapsin and others.

CN102977082A discloses the preparation of isocoumarin derivatives by culturing *Bacillus subtilis* strain PJS. The isocoumarin derivatives display antibacterial activity against gram positive bacteria *Staphylococcus, Klebsiella pneumoniae, Shigella flexneri* and *Streptococcus pneumonia*.

U.S. Pat. No. 9,493,792B1 discloses a process for the production of yellow pigment from *Bacillus* sp. GSK07, isolated from brackish waters of Pondicherry, India. This pigment can be used as a flavoring agent, in cosmetic, chemical and pharmaceutical products and as antioxidant. The pigment produced optimally by cultivation on nutrient broth at 30° C. for 5-7 days and can be extracted by alcohol and has been identified as D-limonene.

Ram et al. [Intr. J. Curr. Pharm. Res. (2017) 9(5) 67-74] disclose the isolation of antibacterial orange fluorescent pigment from *Bacillus endophyticus* AVP(Kf527823). The pigment was extracted using an organic solvent and showed antimicrobial activity against *E. coli* and *Pseudomonas*. The pigment had an adsorption peak at 493 nm and was tentatively identified as a carotenoid. Kumar et al. [Inter. J. Sci. Engin. Res. (2014) 5(4) 1401-1412] disclose the isolation and characterization of the fluorescent *Bacillus endophyticus* AVP9 from chilli rhizosphere peddakurapadu, Guntur district of Andra Pradesh in India. The bacterium has the ability to solubilize phosphate by an acid phosphatase. The ability of the bacteria to solubilize phosphates made it useful as plant growth promotor. Kumar et al. does not disclose any antibacterial activity produced by the bacterium. Magyarosy et al. [Appl. Environ. Microbiol. (2002) 68(8) 4095-4101] disclose the isolation of chlorxanthomycin, a fluorescent chlorinated pentacyclic pyrene from *Bacillus* sp. This material has a UV/Vis absorption spectrum with absorption maximum at 519, 368, and 290 nm, and inhibited the growth of *B. subtilis* and *B. amyloliquefaciens*. Magyarosy et al. does not disclose any compound having activity against *Serratia marcescens*.

Okulate, M. A. [(2009) hypertext transfer protocol secure://-www.mbl.edu/microbialdiversity/files/2012/08/13BolajiFinalReport.pdf] examined the bioactive compound produced in a co-culture of *Bacillus* sp. and *Paenibacillus* sp. The bioactive material in Okulate is protein in nature (e.g. bacteriocin) and was isolated by precipitation with ammonium sulphate.

Gan et al. [Prep. Biochem. Biotechnol. (2018) 48(7)] disclose isolation of *Bacillus endophyticus* SCU-L which is capable of producing silver nanoparticles that are active against *Candida albicans, Escherichia coli, Salmonella typhi* and *Staphylococcus aureus*. The main teaching of Gan et al. is that green synthesis of metal nanoparticles using an extremophiles and Gan does not report any fluorescent activity or activity against Serratia. As compared with *B. endophyticus* DS43, no fluorescent activity was produced by the halotolerant bacterium *B. endophyticus* SCUL, that is normally produced by *B. endophyticus* DS43.

El-Helw et al., J. Appli. Microbiol. (2019) 126 (2): 443-451 (2018) disclose isolation of forty thermophilic bacteria from compost of an aromatic plant. *B. coagulans* and *B. smithii* of the forty bacteria were shown to produce bioactive compounds active against gram positive and gram negative bacteria. Phylogenetic analysis of the two bacteria strain *B. coagulans* and *B. smithii* showed no correlation between the two bacteria and any *B. endophyticus* strain, indicating a clear difference between the two bacterial groups in metabolism and bioactive metabolites production.

Berekaa et al., Inter. J. Agri. Biol. (2016) 18(8), 1232-1236; is concerned with the industrial production of polyhydroxyalkanoate from bacteria. In particular, they disclose several non-pathogenic strains of bacteria including *Bacillus endophyticus* DS43 as suitable for the production of polyhydroxybutyrate. Also, Berekaa et al., 2016 investigated the sensitivity to antibiotics, resistance to heavy metals and possible toxicity of the bacterium before large scale production of the biopolymer. Detailed information about the bacterium and molecular identification of the organism is characterized by 16s rDNA analysis and the sequence of the gene deposited in gene bank under the accession number: KU199806 (NIH, NCBI, PubMed, Genbank, incorporated by reference).

Due to the progressive increase in antibiotic resistance in bacteria such as *Serratia marcescens*, there is a considerable need to identify biological materials useful for controlling and combattin multidrug-resistant microbial pathogens. Such compounds should be substantially non-toxic to humans and/or selectively toxic to a target microorganism such as *Serratia marcescens*. Moreover, there is a need for a simple and commercializable process for safely producing and recovering such antimicrobial or antibacterial compounds.

The inventors have recognized that certain bacilli such as wild-type *Bacillus endophyticus* or the non-hemolytic strain D43 can safely produce compositions that are substantially non-pathogenic to humans, but which kill or inhibit the growth of a spectrum of pathogens including the opportunistic *Serratia marcescens*. These bacilli can be grown in large volumes and are easily processed to yield a fluorescent antibacterial composition. The inventors have also identified culture media and growth conditions that provide superior yields of an active antibacterial composition that is fluorescent under ultraviolet light.

SUMMARY OF THE INVENTION

One aspect of the invention is directed to a method of producing a fluorescent antimicrobial or antibacterial composition by culturing a *Bacillus* species in a suitable medium for a time in the range of 24 h to 96 h at a temperature in the range of 20-40° C. to form a bioactive composition, separating the bioactive composition from the cultured *Bacillus*, and optionally isolating one or more bioactive compound from the bioactive medium; and wherein the *Bacillus* species has S16 RNA having at least 80% sequence identity to SEQ ID NO: 1. Preferably from the standpoint of producing a composition with a higher antibacterial activity, the *Bacillus* is cultured in tryptone soya broth or TSB. In a preferred embodiment, the *Bacillus* species is *Bacillus endophyticus*.

In another preferred embodiment, the *Bacillus endophyticus* is *Bacillus endophyticus* DS43. *Bacillus endophyticus* DS43 is described by accession number DSM 34706 at the DSMZ Patent Depository, Inhoffenstraße 7B, 38124 Braunschweig Science Campus Braunschweig-Süd GERMANY.

In another preferred embodiment, the growth medium is a nutrient broth medium (NB), a Luria-Bertani (LB) medium, or a tryptone soy broth (TSB) medium.

In a more preferred embodiment, the medium is a tryptone soy broth (TSB) medium.

In another preferred embodiment, the medium further comprises a date syrup as a carbon source.

In another preferred embodiment, the date syrup comprises 25. 30, 35, 40, 45 or –50% fructose, 30, 35, 40, 45, or –50% glucose, and 0.1, 0.2, 0.05, 1, 2, 5, 10, 15 to –20% sucrose, each relative to the total volume of the date syrup.

In another preferred embodiment, the date syrup content of a growth medium is 0.5, 1, 2, 3, 4, 5, 6, or –7% v/v relative to a total volume of the growth medium and the bacteria.

In another preferred embodiment, the growth medium further comprising 0.1, 0.2, 0.5, 1, 2, 3, 4, or 5% v/v molasses or palm sugar, relative to the total volume of the growth medium and bacteria.

In another preferred embodiment, the growth medium comprises 0.1, 0.2, 0.5, 1, 2, 3, 4, 5, 6, 7, 8, 9 or 10 g/L of the nutrient broth, 0.1, 0.2, 0.5, 0.75 to –1 g/L of magnesium sulfate heptahydrate, and 1, 2, 3, 4, or –5 mL/L of a trace element solution, and the growth medium has a pH in the range of 3, 4, 5, 6, 7, 8, 9, or 10.0; wherein the trace element solution comprises 0.05, 0.1, 0.2, 0.5, 0.6, 0.7, 0.8, 0.9 to –1 g/L of zinc sulfate heptahydrate, 0.01, 0.02, 0.05, 0.1, 0.2, 0.5, 0.75-1.0 g/L of manganese chloride tetrahydrate, and 0.01, 0.02, 0.05, 0.1, 0.2, 0.5, 0.75 to –1.0 g/L copper sulfate tetrahydrate.

In another preferred embodiment, the nitrogen source is present in the growth medium in an amount of 0.1, 0.2, 0.3, 0.4, to –0.5 wt. % of the total weight of the growth medium.

In another preferred embodiment, the nitrogen source comprises one or more of tryptone, tryptic soy, beef extract, peptone, ammonium salts, and nitrate salts.

In another preferred embodiment, the growth medium further comprises one or more of cysteine, leucine, methionine, tryptophan, histidine, glutamine and proline in an amount in the range of 0.05, 0.1, 0.2, 0.3, 0.4, to 0.5 wt. % of the total weight of the growth medium.

In another preferred embodiment, the culturing comprises growing the bacteria at a growth temperature of 20, 25, 30, 35, 40 or 45° C. Growth may be under static or under agitation, such as undermechanical agitation. Any suitable mode of culturing may be used, including batch, fed batch and continuous culture. Preferably, the culturing is performed under fed-batch conditions and under mechanical agitation, for example on a shaker platform or using magnetic stirring devices.

In another preferred embodiment, the bacteria is cultured for 8, 10, 12, 15, 18, 20, 24, 36, 48, 60, 72, 84 or >84 hours, preferably from about 20-84 hours in a fed-batch phase in which tdate syrup is administered to the cultured bacilli.

In another preferred embodiment, date syrup is administered in a pulse, a shot feeding, a linearly modulated feeding, an exponentially modulated feeding, or a constant feeding during the fed-batch phase.

In another preferred embodiment, isolating the bioactive compound comprises extracting the bioactive compound from the aqueous solution with an organic solvent and optionally further purifying the compound by chromatography.

In one preferred embodiment, a method of producing one or more bioactive compound, comprises culturing *Bacillus endophyticus* in tryptone soy broth (TSB) medium growth medium comprising date syrup as carbon source and nitrogen source for a time in the range of 24 h to 96 h at a temperature in the range of 25-48° C. to form a bioactive composition, separating *Bacillus endophyticus* from the bioactive composition to form a bioactive medium, and isolating one or more bioactive compound from the bioactive medium; wherein the one or more bioactive compound has bacteriocidal activity against at least against *Serratia marcescens* and *Staphylococcus aureus*, and wherein the *Bacillus endophyticus* has 16s rDNA having at least 90% sequence identity to SEQ ID NO: 1.

Another aspect of the invention is directed to a method for treating a patent having a bacterial infection comprises administering to a patient a pharmaceutical composition comprising a preparation of one or more bioactive compound prepared by the method of claim 1.

In another preferred embodiment, the patient is infected with a bacterium from the genus *Serratia, Staphylococcus, Bacillus, Pseudomonas,* or *Escherichia*.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
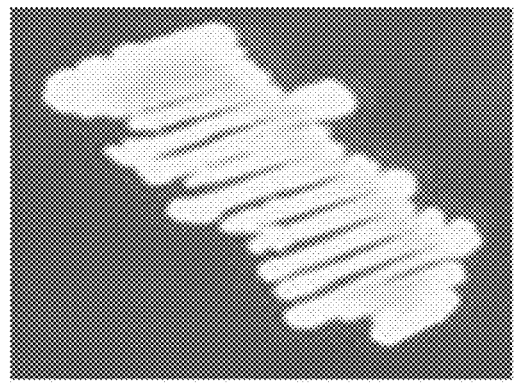
FIG. 1 shows the yellow fluorescence produced by *B. endophyticus* DS43 under UV light.

Embodiments of the present disclosure will now be described more fully hereinafter with reference to the accompanying drawings, in which some, but not all embodiments of the disclosure are shown. The present disclosure will be better understood with reference to the following definitions.

An aspect of the present disclosure relates to a method for producing one or more bioactive compounds in bacteria of a *Bacillus* species. In one embodiment, the *Bacillus* species is collected from Dammam City, Saudi Arabia. *Bacillus* is a genus of gram positive, rod-shaped (*Bacillus*) bacteria and a member of the phylum Firmicutes. *Bacillus* species can be obligate aerobes, which are oxygen reliant, or facultative anaerobes having the ability to be aerobic or anaerobic. *Bacillus* species may be obtained from soil, deep oceans, ocean vents, aquatic areas, waste water treatment reservoirs, or sewage reservoirs. *Bacillus* species employed in the presently disclosed method may include, but are not limited to *Bacillus subtilis, Bacillus pumilus, Bacillus alvei, Bacillus brevis, Bacillus megaterium, Bacillus circulans, Bacillus amyloliquefaciens,* and *Bacillus thuringiensis*.

As used herein 16s ribosomal RNA (encoded by 16srDNA) is a component of the 30s small subunit of a prokaryotic ribosome that binds to the Shine-Dalgarno sequence. It is used in constructing phylogenic tree within a family of bacteria, due to the slow rates of evolution of 16s rDNA. In some embodiments, the *Bacillus* species has a 16s rDNA sequence having at least 50%, at least 60%, at least 70%, at least 80%, at least 85%, at least 90%, at least 91%, at least 92%, at least 93%, at least 94%, at least 95%, at least 96%, at least 97%, at least 98%, 99, 99.5% and at least 99.9% sequence identity to 16s rDNA of *B. endophyticus*, preferably *B. endophyticus* SD43 described by SEQ ID NO: 1. Alternatively, a strain may have 16s RNA that has 1, 2, 3, 4, 5, 6, 7, 8, 9, 10, 11, 12, 13, 14 or 15 deletions, substitutions or insertions compared to that of *Bacillus endophyticus* DS43 with the 16S rDNA accession number deposited in GenBank #KU199806 (last version of sequence incorporated by reference).

BLASTN may be used to identify a polynucleotide sequence having the percentage of sequence similarity or sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are described by and incorporated by reference to hypertext transfer protocol:-//blast.ncbi.nlm.nih.gov/Blast (last accessed Nov. 16, 2020).

The sequence of, and degree of sequence identity between two rDNA or rRNA sequences may be determined via hypertext transfer protocol secure://support.illumina.com/content/dam/illumina-support/documents/documentation/chemistry_documentation/16s/16s-metagenomic-library-prep-guide-15044223-b.pdf (last accessed Sep. 3, 2019, incorporated by reference).

In some embodiments, the *Bacillus* species has a 16s rDNA or rRNA sequence which hybridizes to SEQ ID NO: 1 under low, preferably medium, preferably medium high, preferably high stringent conditions. The term "low stringency conditions" means, for probes having at least 100 nucleotides in length complementary to SEQ ID NO: 1 or part thereof, prehybridization and hybridization at 42° C. in 5×SSPE, 0.3% SDS, 200 µg/ml sheared and denatured salmon sperm DNA, and 25% formamide, following standard blotting procedures for 12 to 24 hours. The carrier material is finally washed three times—each for 15 minutes using 2×SSC, 0.2% SDS at 50° C. The term "medium stringency conditions" means for probes having at least 100 nucleotides in length complementary to SEQ ID NO: 1 or part thereof, prehybridization and hybridization at 42° C. in 5×SSPE, 0.3% SDS, 200 µg/ml sheared and denatured salmon sperm DNA, and 35% formamide, following standard blotting procedures for 12 to 24 hours. The carrier material is finally washed three times—each for 15 minutes using 2.times. SSC, 0.2% SDS at 55° C. Medium-high stringency conditions: The term "medium-high stringency conditions" means, for probes having at least 100 nucleotides in length complementary to SEQ ID NO: 1 or part thereof, prehybridization and hybridization at 42° C. in 5×SSPE, 0.3% SDS, 200 µg/ml sheared and denatured salmon sperm DNA, and 35% formamide, following standard blotting procedures for 12 to 24 hours. The carrier material is finally washed three times—each for 15 minutes using 2×SSC, 0.2% SDS at 60° C. The term "high stringency conditions" means, f for probes having at least 100 nucleotides in length complementary to SEQ ID NO: 1 or part thereof, prehybridization and hybridization at 42° C. in 5×SSPE, 0.3% SDS, 200 µg/ml sheared and denatured salmon sperm DNA, and 50% formamide, following standard blotting procedures for 12 to 24 hours. The carrier material is finally washed three times—each for 15 minutes using 2×SSC, 0.2% SDS at 65° C.

In some embodiments, the *Bacillus* of the present disclosure may be combined with non-*Bacillus* bacteria such as, but not limited to *Aeromonas hydrophila*, *Thiococcus pfennigii*, and *Pseudomonas putida* with the objective of enhancing the production of the bioactive compound(s) production.

The method includes culturing the bacteria of the *Bacillus* species in a growth culture medium, said *Bacillus* species biosynthetically producing at least one bioactive compound, and isolating the bioactive compound from the *Bacillus*.

As used herein, the term "bioactive compound" is a chemical compound isolated from a culture of a *Bacillus* species having at least one or more activity such as but not limited to antibacterial activity, antifungal activity, antiviral activity, anticancer activity, antimalarial activity, psychotropic activity, neurotropic activity, and the like. In some embodiments, the *Bacillus* may produce a fluorescence compound having a characteristic absorption in the UV/Vis spectrum at about 518 nm. The extracted composition exhibits bright yellow fluorescence when exposed to a UV lamp at 360 nm. Spectroscopic analysis of the fluorescence compound from *Bacillus endophyticus* DS43 with the 16S rDNA accession number deposited in GenBank #KU199806, revealed a broad absorption peak in the UV/Vis spectrum at 518 nm.

The fluorescent antibacterial composition as disclosed herein may be biostatic or biocidal against *Serratia* and other gram negative bacteria such as *Klebsiella* sp, *Pseudomonas* sp, *Escherichia* as well against gram positive bacteria such as *Staphylococcus*, *Streptococcus*, or *Bacillus* for example, it can exert antimicrobial effects on *S. aureus*, *Bacillus megaterium*, *Bacillus antracis*.

The growth medium of the method may be any medium comprising a carbon source and nitrogen source. One or more carbon sources such as but not limited to glucose, sucrose, fructose, maltose or a mixture thereof. In a preferred embodiment the growth medium is a date syrup or molasses that is present in the culture medium. Similarly, one or more nitrogen sources such as but not limited to tryptone, beef extract, peptone, ammonium salts, and nitrate salts is used to culture the bacteria. Examples of ammonium and nitrate salts include, but are not limited to ammonium nitrate, ammonium sulfate, ammonium chloride, sodium nitrate, potassium nitrate and the like. The nitrogen source in the growth medium is preferably present in an amount in the range of 0.01-1.0 wt. %, preferably 0.05-0.5 wt. %, preferably 0.08-0.4 wt. %, preferably 0.1-0.2 wt. % of the total weight of the culture medium. In addition, the culture medium may be supplemented with at least one or more essential and non-essential amino acids. As used herein "essential amino acids" are histidine, isoleucine, leucine, lysine, methionine, phenylalanine, threonine, tryptophan, valine and arginine. Alanine, aspartic acid, cysteine, glutamic acid, glutamine, glycine, proline, serine, tyrosine, and asparagine are considered non-essential amino acids. In one embodiment, the growth medium comprises cysteine, leucine, methionine, tryptophan, histidine, glutamine and proline. The amino acids are added to the growth medium in an amount in the range of 0.01-1.0 wt. %, preferably 0.05-0.5 wt. %, preferably 0.08-0.4 wt. %, preferably 0.1-0.2 wt. % of the total weight of the culture medium.

The culture medium may be any commercially available growth media such as but not limited to, nutrient broth medium (NB) [5 g/L peptone, 1 g/L beef extract, 2 g/L yeast extract and 5 g/L NaCl]; Luria-Bertani (LB) medium [10 g of tryptone, 10 g of NaCl, and 5 g yeast extract in 900 mL water], and tryptone soy broth (TSB) medium is [17 g of tryptone, 3 g of soy broth, 5 g of Na Cl, 2.5 g dipotassium phosphate, 2.5 g of glucose in a liter of water]. The commercial growth medium may be used as is, or supplemented with carbon source and/or nitrogen source including essential and nonessential amino acids. Other medium may be used constituted from locally abandoned products such as but not limited to meet and poultry byproducts, soy byproducts, starch, date syrup, molasses, and food waste. In some embodiments, the growth medium may be a mixture of commercial preparation of a growth medium supplemented with cheap ingredient of carbon source and/or nitrogen source. The growth media may have a pH in the range of 3-10, preferably 4-9, preferably 5-8, preferably 5.5-7.5.

In some embodiments of the method, date syrup is a source of food in the growth medium for the bacteria to produce the bioactive compound. The volume of the date syrup is in a ratio relative to a volume of the growth medium and the bacteria of about 0.5%-7%, about 1%-5%, or about 2%-3%. In some embodiments of the method, the date syrup may include sugars, proteins, and ash. A sugar volume relative to a total volume of date syrup may be about 0.5%-95%, about 1%-90%, about 5%-85%, about 10%-80%, about 15%-75%, about 20%-70%, about 30%-60%, or about 40%-50%. A protein volume relative to the total volume of date syrup may be about 1%-10%, about 1.5%-9.5%, about 2%-8%, about 2.5%-7%, about 3%-6%, or about 4%-5%. An ash volume relative to the total volume of date syrup may be about 0.1%-5%, about 0.5%-4.5%, about 1%-4%, about 1.5%-3.5%, or about 2%-3%. The sugars in date syrup may include, but are not limited to fructose, glucose, and sucrose. In the present method, the date syrup may include a volume of fructose relative to the total volume of date syrup of about 15%-20%, or about 17%-18%.

In the present method, the date syrup may include a volume of glucose relative to the total volume of date syrup of about 20%-40%, about 22%-38%, about 25%-35%, or about 28%-32%. In the present method, the date syrup may include a volume of sucrose relative to the total volume of date syrup of about 0.1%-50%, about 0.5%-45%, about 1%-35%, about 5%-30%, about 10%-25%, or about 15%-20%. The date syrup may further include tannins, citric acid, and pectin at a volume relative to the total volume of date syrup of about 0.1%-10%, about 0.5%-8%, about 1%-5%, or about 2%-4%. In some embodiments of the method, the date syrup comprises at least one polyphenol selected from the groups consisting of caffeoylshikimic acid hexoside, caffeoyl-sinapoyl monohexoside, and caffeoyl-sinnapoyl dihexoside. The date syrup may include a volume of polyphenol relative to the total volume of date syrup of about 0.1%-20%, about 0.5%-18%, about 1%-15%, about 2%-12%, about 3%-10%, about 4%-9%, about 5%-8%, or about 6%-7%. In some embodiment of the method, the date syrup may further comprise a fatty acid such as palmitic acid, linoleic acid, or linolenic acid. The date syrup may include a volume of fatty acids relative to the total volume of date syrup of about 0.1%-5%, about 0.25%-4.5%, about 0.5%-4%, about 0.75%-3.5%, about 1%-3%, or about 1.5%-2.5%.

In some embodiments of the method, the growth medium may further include molasses and/or palm sugar. Either molasses and/or palm sugar may be in a volume/volume ratio relative to a volume of a culture of the bacteria of about 0.1%-5%, about 0.5%-5%, about 1%-4%, or about 2%-3%.

In some embodiments of the method, a level of dissolved oxygen may be between about 0.1%-25%, about 0.5%-15%, about 1%-10%, about 5%-8%, or about 6%-7% of the total weight of the culture medium. The level of oxygen may directly impact the production efficiency of the bioactive compound in the bacteria.

The growth media in which the bacteria grows and expresses the bioactive compound may include additional nutrients and minerals. In some implementations of the method, the growth medium may include nutrient broth, magnesium sulfate heptahydrate, and/or a trace element solution. The growth media may further include ammonium sulfate, disodium phosphate dodecahydrate, calcium chloride dihydrate, and/or ferrous sulfate heptahydrate. The nutrient broth may have a concentration of about 0.1 g/L-10 g/L, about 0.5 g/L-9.5 g/L, about 1 g/L-9 g/L, about 1.5 g/L-8.5 g/L, about 2 g/L-8 g/L, about 2.5 g/L-7.5 g/L, about 3 g/L-7 g/L, about 3.5 g/L-6.5 g/L, about 4 g/L-6 g/L, or about 4.5 g/L-5.5 g/L per volume of the growth medium. The ammonium sulfate may have a concentration of about 0.1 g/L-5 g/L, about 0.5 g/L-4.5 g/L, about 1 g/L-4 g/L, about 1.5 g/L-3.5 g/L, about 2 g/L-3 g/L per volume of the growth medium. The disodium phosphate dodecahydrate may have a concentration of about of about 0.1 g/L-5 g/L, about 0.5 g/L-4.5 g/L, about 1 g/L-4 g/L, about 1.5 g/L-3.5 g/L, about 2 g/L-3 g/L per volume of the growth medium. The magnesium sulfate heptahydrate may have a concentration of about of about 0.1 g/L-1 g/L, about 0.2 g/L-0.9 g/L, about 0.3 g/L-0.8 g/L, about 0.4 g/L-0.7 g/L, or about 0.5 g/L-0.6 g/L per volume of the growth medium. The calcium chloride dihydrate may have a concentration of about of about 0.1 g/L-2 g/L, about 0.2 g/L-1.9 g/L, about 0.3 g/L-1.8 g/L, about 0.4 g/L-1.7 g/L, about 0.5 g/L-1.6 g/L, about 0.6 g/L-1.5 g/L, about 0.7 g/L-1.4 g/L, about 0.8 g/L-about 1.3 g/L, about 0.9 g/L-1.2 g/L, about 1 g/L-1.1 g/L per volume of the growth medium. The ferrous sulfate heptahydrate may have a concentration of about 0.001 g/L-2 g/L, about 0.05 g/L-1.9 g/L, about 0.1 g/L-1.8 g/L, about 0.5 g/L-1.7 g/L, about 0.6 g/L-1.6 g/L, about 0.7 g/L-1.5 g/L, about 0.8 g/L-1.4 g/L, about 0.9 g/L-1.3 g/L, or about 1 g/L-1.2 g/L per volume of the growth medium. The trace element solution may have a volume/volume ratio in the growth medium in the range of about 1 mL/L-5 mL/L, about 1.5 mL/L-4.5 mL/L, about 2 mL/L-4 mL/L, or about 2.5 mL/L-3.5 mL/L. The growth medium may be a pH of about 6.9-7.4, about 6.95-7.35, about 7-7.3, about 7.05-7.25, or about 7.1-7.2.

In some embodiments of the method, the trace element solution may include, but is not limited to zinc sulfate heptahydrate, manganese chloride tetrahydrate, and copper sulfate tetrahydrate. The trace element solution may further include boric acid, cobalt chloride hexahydrate, and sodium molybdate dihydrate. Trace elements may be important to the bacteria health by providing structural support to nucleic acids or regulation and activity of bacterial enzymes. A concentration of the zinc sulfate heptahydrate in the trace element solution may be about 0.05 g/L-1 g/L, about 0.1 g/L-0.9 g/L, about 0.2 g/L-0.8 g/L, about 0.3 g/L-0.7 g/L, or about 0.4 g/L-0.6 g/L. A concentration of the boric acid in the trace element solution may be about 0.1 g/L-1.5 g/L, about 0.2 g/L-1.4 g/L, about 0.3 g/L-1.3 g/L, about 0.4 g/L-1.2 g/L, about 0.5 g/L-1.1 g/L, about 0.6 g/L-1.0 g/L, or about 0.7 g/L-0.9 g/L. A concentration of the manganese chloride tetrahydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L. A concentration of the cobalt chloride hexahydrate in the trace element solution may be about 0.1 g/L-1.5 g/L, about 0.2 g/L-1.4 g/L, about 0.3 g/L-1.3 g/L, about 0.4 g/L-1.2 g/L, about 0.5 g/L-1.1 g/L, about 0.6 g/L-1.0 g/L, or about 0.7 g/L-0.9 g/L. A concentration of the copper sulfate tetrahydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L. A concentration of the sodium molybdate dihydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L.

In some embodiments of the method the growth media may further include non-sugar ingredients, which may enhance and support the bioactive compound production by *Bacillus* sp. The non-sugar ingredients may include, but are not limited to vitamin B complex, calcium, phosphate, iron, and magnesium. Each non-sugar ingredient may be included in the growth media in a concentration of about 0.001-1.0 g/L, about 0.01 g/L-0.9 g/L, about 0.1 g/L-0.8 g/L, about 0.3 g/L-0.7 g/L, about 0.4 g/L-0.6 g/L. The enhancement of PHAs produced as a result of adding at least one non-sugar ingredient relative to PHAs produced without adding the non-sugar ingredient to the growth media may be an increase of 1%-20%, 2%-18%, 5%-15%, or 8%-12%.

In some embodiments of the method, the culturing includes growing the bacteria at a growth temperature in the range of 25° C.-40° C., preferably about 26° C.-39° C., about 27° C.-38° C., about 30° C.-37° C. The culture may be incubated under static condition or shaken in an orbital shaker at a rate in the range of 10-600 rpm, preferably 40-500 rpm, preferably 60-400 rpm, preferably 80-300 rpm, preferably 100-200 rpm. In some other embodiments, the culture is incubated with agitation in a fed-batch process vessel. The agitation may be accomplished by methods including, but not limited to mixing by baffle attached to an impeller, pulsed-jet mixer, or close-clearance mixers. For bacterial cultures, mixing increases circulation and reduces settling in the fed-batch process vessel.

In some embodiments of the method, the culturing further includes growing the bacteria in a fed-batch phase for about 20 hours-84 hours, about 22 hours-72 hours, about 24 hours-68 hours, about 26 hours-66 hours, about 28 hours-64 hours, about 30 hours-62 hours, about 32 hours-60 hours, about 34 hours-58 hours, about 36 hours-56 hours, about 38 hours-54 hours, about 40 hours-52 hours, about 42 hours-50 hours, or about 44 hours-48 hours. During the fed-batch phase, the date syrup and/or molasses is administered to the bacteria at a final concentration in the growth media of about 5 g/L-100 g/L, 10 g/L-90 g/L, 20 g/L-80 g/L, 30 g/L-70 g/L, 40 g/L-76 g/L, or about 5 g/L.

In some embodiments of the method, the level of the date syrup relative to a volume of the bacteria in the fed-batch process vessel may be a volume/volume ratio of about 0.1%-10%, about 0.5%-8%, about 1%-6%, about 1.1%-5%, about 1.25%-4%, about 1.5%-3.5%, about 1.75%-2.75%, or about 2%-2.5%.

In some embodiments of the method, the date syrup may be administered in a pulse feeding, a shot feeding, a linearly modulated feeding, an exponentially modulated feeding, or a constant feeding during the fed-batch phase. The pulse feeding may be described as administering date syrup to the bacteria in an interrupted sequence in which a concentration administered at each pulse is constant. The shot feeding may be described as administering date syrup in one dose to the bacteria. The linearly modulated feeding may be described as uninterruptedly introducing date syrup to the bacteria in a concentration that linearly increases or linearly decreases over a period of time. The exponentially modulated feeding may be described as uninterruptedly introducing date syrup to the bacteria in a concentration that exponentially increases or exponentially decreases over a period of time. The constant feeding may be described as maintaining a continuous administration of an unchanging concentration of the date syrup over a period of time.

After the fed-batch phase duration, the bioactive compound may be preserved from degradation by reducing the growth temperature in the fed-batch process vessel containing the cultured bacteria. In some implementations, the growth temperature is reduced to an ambient temperature after the fed-batch phase of about 20° C.-25° C., about 21° C.-24° C., or about 22° C.-23. ° C.

The disclosed method for the production of bioactive compound may be carried out in laboratory scale reactor in a volume 50 mL-10 L batches, pilot plant scale of 100 L-1000 L batches, or industrial scale of more than 2000 L batches. Generally, the *Bacillus* species is cultured overnight at an optimal condition and added to a reactor in an amount of at least (v/v) 0.1%, preferably 0.2%, preferably, 0.2%, preferably 0.3%, preferably 0.4%, preferably 0.5%, preferably 0.7%, preferably 1.0%, preferably 1.2%, preferably 1.5%.

Once the growth temperature is reduced, the *Bacillus* sp. cells are isolated from the culture medium by settling the bacteria, preferably by centrifugation, or combination thereof, and discarding the supernatant. In some embodiments, the cells are separated from the culture medium by centrifugation at 2000-10,000 rpm, preferably 4000-9000 rpm, preferably 6000-8000 rpm, preferably about 7500 rpm for a period of time in the range of 5-30 min, preferably 7-20 min, preferably 10-15 min. In some embodiments, following separating the bacteria from the growth media, the bacterial cells are re-suspended in an organic solvent such as, but not limited to acetone, methanol, ethanol, propanol, isopropanol, acetonitrile, tetrahydrofuran, and dioxane. The suspended cells in organic solvent may further sonicated to disperse the bioactive compound into the solution. The sonicating may be at a frequency of about 15 kHz-50 kHz, about 20 kHz-40 kHz, about 25 kHz-35 kHz, or about 28 kHz-32 kHz. Finally the cell debris is separated from the organic solvent by centrifugation at 5000-15,000 rpm, preferably 7000-12,000 rpm, preferably 9000-11,000 rpm, preferably about 10,000 rpm for a period of time in the range of 5-30 min, preferably 7-20 min, preferably 10-15 min and the bioactive compound is obtained by evaporating the organic solvent.

In some other embodiments, following separating the bacteria from the growth media, the bacterial cells are re-suspended in a detergent media. The detergent media may include, but is not limited to at least one detergent selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-.beta.-D-thioglucopyranoside, a chaotropic agent, and a buffer.

The chaotropic agent is a substance which disrupts the structure of, and denatures, macromolecules such as proteins and nucleic acids (e.g. DNA and RNA). Chaotropic solutes increase the entropy of the system by interfering with intramolecular interactions mediated by non-covalent forces such as hydrogen bonds, van der Waals forces, and hydrophobic effects. An increase in chaotropic solutes in a biological system will denature macromolecules, reduce enzymatic activity and induce stress on a cell.

The chaotropic agent may include, but is not limited to butanol, ethanol, guanidinium chloride, lithium perchlorate lithium acetate, magnesium chloride, phenol, propanol, sodium dodecyl sulfate, thiourea, or urea. The buffer may be a pH of about 5-8, about 5.5-7.5, about 6-7. In some embodiments of the method, the detergent media further includes a lysozyme, which is an enzyme that catalyzes reactions that break down a bacterial cell wall. The detergent media may disrupt and weaken the cell walls and membranes of the bacteria, to break open bacteria and the content of the cells. After reheating, sonicating the lysed bacteria in the detergent media may further disperse the bioactive compound into the solution. The sonicating may be at a frequency of about 15 kHz-50 kHz, about 20 kHz-40 kHz, about 25 kHz-35 kHz, or about 28 kHz-32 kHz.

The solid debris may be separated from the cell lysate by filtering, centrifugation, or settling. In some embodiments, the method include adding a secondary detergent to the lysed bacteria in the detergent media to additionally break down membranes and dissociate agglomerated proteins around the inclusion body, before separating the supernatant from the lysed bacteria. The secondary detergent is selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-.beta.-D-thioglucopyranoside. A second sonicating may follow the addition of the secondary detergent, as described herein.

Upon collecting the supernatant, one or more bioactive compound may be extracted from the aqueous medium by an organic solvent or loaded on a reverse phase column and eluted from the column with an aqueous organic solvent such as acetonitrile in water. Finally, the solvent is evaporated by well-known methods in the art to recover the bioactive compound.

Once the one or more bioactive compound is isolated, it may undergo further purification by well-known methods in the art such as crystallization, chromatography on silica column, reverse phase column, or ion exchange column. The chemical structure and physical properties of the bioactive compound may be determined by mass spectroscopy, $^1$HNMR, $^{13}$CNMR, FT-IR spectroscopy, UV/Vis absorption spectroscopy, and fluorescence spectroscopy as well as elemental analysis and other methods well-known to those skilled in the art.

In some additional embodiments of this method the *Bacillus endophyticus* is cultured in a medium that contains a carbon or nitrogen source other than starch, casein or gelatin; in a medium containing citrate or gluconate; in a medium containing at least one of L-arabinose, D-glucose, meso-inositol, D-mannitol, D-mannose, melibiose, D-rhamnose, ribose or sucrose; and/or in a medium containing less than 10 wt % NaCl. In other embodiments of this method the *Bacillus endophyticus* is cultured under microaerophilic conditions under a concentration of oxygen ranging from 0, >0, 1, 2, 3, 4, 5, 6, 7, 8, 9, 10, 11, 12, 13, 14, 15, 16, 17, 18, 19, 20 or <21%. In some embodiments, the bacteria may be cultured in a medium containing antioxidants, such as cysteine, mercaptoethanol, DTT, glutathione, catechin hydrate, quercetin dehydrate, chlorogenic acid, vitamin C, or vitamin E.

In some embodiments, this *Bacillus endophyticus* disclosed herein may be cultured at a temperature ranging from 20-40° C., for about 24-72 hours, using an inoculum size of 0.5 to 1.5% v/v, at various pHs including 3, 4, 5, 6, 7, 8, 9 or 10. They may be cultured using various carbon sources including glucose, sucrose, fructose, maltose or the most common and cheap raw material in Saudi Arabia the date syrup or DEB S; or various nitrogen sources such as tryptone, beef extract, peptone, ammonium salts, nitrate salts which may be present at a final conc. 0.05, 0.1, 0.15, 0.2, 0.25, 0.3 wt % or greater, they may contain various amino acids, such as cysteine, leucine, methionine, tryptophan, histidine, glutamine and proline typically at a final concentration in the culture medium of 0.05, 0.1, 0.15, 0.2, 0.25, 0.3 wt. % or greater. As disclosed herein the wt. % unless otherwise specified is based on the total weight of the growth medium.

Suitable media include nutrient broth, tryptone soya broth or tryptic soy broth (TSB). Cultivation may be static or under agitation such as shaking an 80, 100, 120, 150-200 rpm.

In some embodiments, the fluorescent compound is extracted from the cells by the use of an organic solvent or using organic solvents with different polarities such as acetone, methanol or ethanol. Cells may be lysed prior to extraction.

A typical Luria broth (LB) contains 10 g of tryptone, 5 g of yeast extract and 10 g of NaCl in 1 L of water.

TSB or tryptic/tryptone soy broth typically contains 17 g of tryptone, 3 g of soy, 5 g of NaCl, 2.5 g of dipotassium phosphate, 2.5 g of glucose in 1 L of water. As disclosed herein cultivation of *Bacillus* on TSB, which contains phosphate and glucose, yielded a composition with higher antibacterial properties as measured by the size of the inhibition zone. Therefore its use, or use of a medium containing phosphorous and a glucose or other sugars, such as those present in date syrup, is preferred. Nutrient broth as described herein contains 5 g peptide, 3 g beef extract, 3 g NaCl in 1 L of water.

In some embodiments, the fluorescent antibacterial composition may be extracted from the culture medium, but preferably it is extracted from the cultured bacterial cells.

Means for disrupting bacteria such as *Bacillus endophyticus* are known in the art and include, but are not limited to sonication, French pressing, homogenizer treatment, microfluidization, bead beating, cryopulverization, nitrogen decompression (or decompression with carbon dioxide, nitrous oxide, carbon monoxide or other gases), osmotic shock, and enzyme treatment. During decompression nitrogen gas is preferred because it is non-reactive and does not alter the pH of the disrupted cells and can provide a more uniform disrupted product than other modes of disruption. Solid and liquid fractions of disrupted cells may be further separated by filtration or centrifugation or by other methods known in the art. Water soluble and hydrophobic fractions of disrupted cells may be separated by extraction with organic or aqueous solvents. Common extractants include ethyl acetate<acetone<ethanol<methanol<acetone:water (7:3) <ethanol:water (8:2)<methanol:water (8:2)<water) in increasing order of polarity according to the Hildebrand solubility parameter. Such solvents include n-pentane, n-hexane, methanol, ethanol, propanol, butanol, diethyl ether, ethyl acetate, chloroform, dichloromethane, and acetone. In some preferred embodiments, extraction of the fluorescent antibacterial composition is performed using acetone or methanol.

Once cells are disrupted or once an extract composition is produced, it may be refrigerated, frozen, dried or kept under an inert atmosphere not containing oxygen. An extract can be reduced to a dried form using a centrifugal evaporator or a freeze-drier.

A concentrated or dried composition as disclosed herein may be reconstituted in water or another suitable buffer or carrier to contain 0.001, 0.002, 0.005, 0.01, 0.02, 0.05, 0.1, 0.2, 0.5, 1, 2, 5, 10 or >10 wt % of the concentrated or dried fluorescent material.

As used herein, the fluorescent material may be in the form of a purified compound, for example in a form where at least 50, 60, 70, 80, 90, 95, 99, <100, or 100% of the fluorescent material has been separated from other components of the microorganism in which it was produced. It may also be in a form of a composition which consists of, consists essentially of, or comprises a fluorescent material(s) or compound(s).

Gram negative bacteria which may be treated with a composition as disclosed herein include enterobacteria such as *Serratia* which are a genus of Gram negative, facultative anaerobic, rod-shaped bacteria. *Serratia* species include *S. Aquatilis, S. entomophila, S. ficaria S. fonticola, S. glossinae, S. grimesii, S. liquefaciens, S. marcescens, S. myotis, S. nematodiphila, S. odorifera, S. plymuthica, S. proteamaculans, S. quinivorans, S. rubidaea, S. symbiotica*, S. ureilytica, S. vespertilionis.

Infection with *Serratia* often results in one or more of the following symptoms: chills, fever, sepsis (pus-forming bacteria in the body), infection (by pathogenic microorganisms), nausea, vomiting, shock, convulsions or bacteremia (bacteria in the blood), or urinary tract infections. Administration of the antibacterial composition as disclosed herein may reduce the intensity of, or the risk of developing, one or more of these symptoms. Modes of administration for the composition disclosed herein include topical, for example, on or into a wound or burn, onto a mucous membrane, oral, or in some cases parenteral to subjects not allergic or sensitive to the composition.

Another aspect of the invention is directed to a composition comprising, consisting essentially of, or consisting of a fluorescent material or composition as disclosed herein and at least one oil, grease, alcohol, wax, surfactant, UV protectant, vitamin, amino acid, antibiotic, gel, propellant, polymer, or solid support. In some embodiments this composition is the form of an emulsion, lotion, paste, glue, salve, ointment, sunscreen, cosmetic, gel, liquid bandage, or foam. Compositions containing a fluorescent material or composition as disclosed herein may contain other excipients, adjuvants or carriers including medium chain triglycerides, ingestible oils such as coconut oil, soybean oil, canola oil, olive oil, or other vegetable oils, water, hydroxypropylcellulose, gelatin, or surfactants, such as lecithin or a poly sorbate.

It may be formulated in a form suitable for administration including as a pill, tablet, capsule, gel caplet, soft gel, lozenge, cream, rinse, ointment, gel, paste, water-based cream, emulsions, serum, spray, suppository, ovules, powder, mist, aerosol or other inhalable form, or transdermal patch.

In another embodiment the composition disclosed herein will form part of a wound dressing, bandage, patch, gauze, suture, surgical tape, or wipe.

In another embodiment, the composition disclosed herein further includes at least one antimicrobial, antiviral or antibacterial material.

It may also be formulated as part of a drink, drink or shake mix or food, or animal feed.

Alternatively, the antibacterial composition as disclosed herein may be incorporated into cleaning solution or sanitary product, for example, that is used to sanitize residential (e.g, kitchen, bathroom, nursery), commercial (e.g. restaurant, restroom, gym) or hospital or ambulance surfaces. Such a product may contain one or more surfactants such as a cationic, nonionic or anionic detergent, soaps, a preservative such as EDTA, or an organic solvent such as ethanol or isopropanol. In some embodiments, the fluorescent composition of the invention may be in the form of a gel, foam, spray, liquid solution or in a particulate form such as a powder, for example, the fluorescent composition may be an ingredient in a hand sanitizer.

Advantageously, the presence of a sanitary product containing the fluorescent composition of the invention on a surface may be detected under UV illumination. Thus, in some embodiments, the fluorescent composition alone or admixed with other microbicidal materials may be used to detect exposure of a surface, including skin, medical supplies or equipment, to a sanitary product containing the fluorescent composition. In one embodiment, the fluorescent composition in incorporated into a skin car product, such as a baby lotion, to help identify areas that have been covered with the skin care product and areas that have not.

Example 1

Isolation and Characterization of *Bacillus endophyticus* DS43

Soil and sewage samples were collected in sterile containers from Dammam, Al-Khobar, Qateif and Al-Hassa in the Eastern Province of Saudi Arabia. Isolation of bacteria was carried out as following: soil or sewage sample was diluted in sterile distilled water and 0.1 mL was plated on nutrient agar (NA plates) with composition of 5 g/L Peptone; 3 g/L beef; 5 g/L NaCl 5, and 15 g/L agar. Separate colonies were isolated and further purified as describe in Berekaa et al. [Int. J. Agr. Biol (2016) 18 (6) 1232-1236; httprotocol://-www.fspublishers.org/published_papers/4575_pdf—incorporated herein by reference in its entirety]. The purified strains were subjected to screening for polyhydroxybuerate (PHB) production after cultivation on three different mineral salts production media: M1 or modified E2 medium [Berekaa and Al-Thawadi Afr. J. Microbiol. Res. (2012) 6, 838-845—incorporated herein by reference in its entirety]; M2 medium comprising 2 g/L ammonium sulfate, 6.67 g/L $KH_2PO_4$, 4 g/L $(NH_4)H_2PO_4$, and 0.8 g/L $MgSO_4.7H_2O$ in addition to 5 mL/L of trace elements solution comprising 5 g/L HCl, 10 g/L $FeSO_4.7H2O$, 2 g/L $CaCl_2$, 0.5 g/L $MnSO_4.4H_2O$, 2.2 g/L $ZnSO_4.7H_2O$, 1.9 g/L $CuSO_4.5H_2O$, 0.1 g/L $(NH_4)Mo_7O_{24}$, 0.02 g/L $Na_2B_4O_7.10H_2O$; and M3 medium comprising 10 g/L glucose, 2 g/L ammonium sulfate, 0.5 g/L $KH_2PO_4$, 0.2 g/L $MgSO_4.7H_2O$, 0.1 g/L NaCl, 2.5 g/L peptone, and 2.5 g/L yeast extract, at 37° C. After sterilization of the media, filtered and a sterilized stain solution was added. Two stain solution were used. One stain solution contained 0.3 g/L Sudan Black B in 70% ethanol and the other stain solution contained 0.5 μg/mL Nile Red A in DMSO (Berekaa et al. 2016). Positive strains displayed blue-black colonies with Sudan black stain and red fluorescence after staining with Nile Red A and irradiating with UV light.

Figure 3:
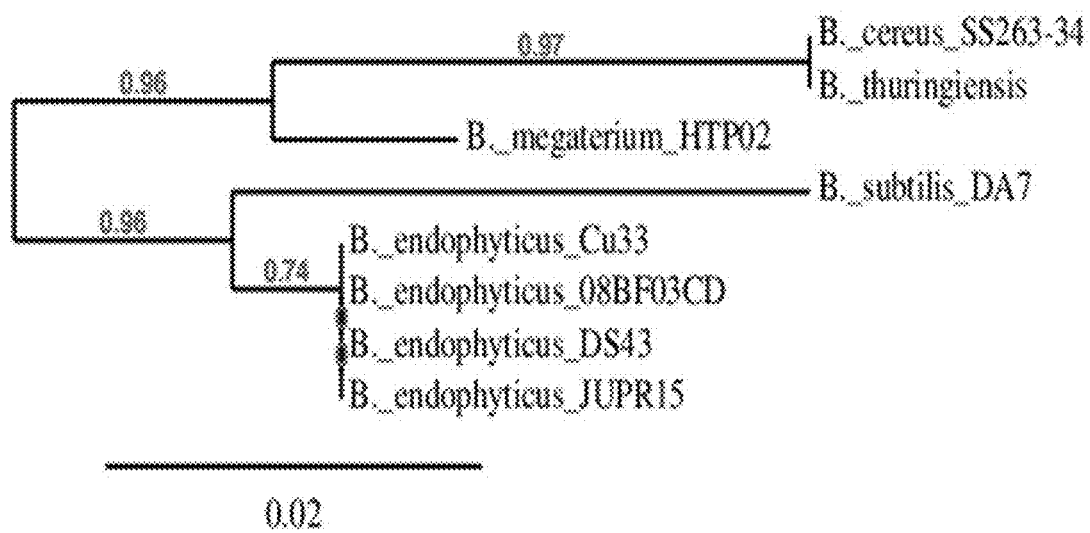
FIG. 3 shows a phylogenetic tree for 16S rRNA of *B. endophyticus* DS43 of SEQ ID NO: 1 in relation to other Bacilli, the numbers in the Phylogram nodes indicate the value of bootstrap analysis based on 16S rRNA nucleic acid sequence.

Among the screened bacteria, 16 strains showed clear positive results with both dyes, and thus, chosen for further investigation. Molecular identification by 16S rRNA analysis indicated that most of the isolated strains are bacilli belong mainly to members of *Bacillus cereus* group, *B. megaterium*, *B. flexus*, *B. endophyticus*, and *B. aryabhattai*. *B. endophyticus*. In particular, *B. endophyticus* DS43 16S rDNA was isolated and sequenced. The 16s rDNA has the nucleic acid sequence of SEQ ID NO: 1, which has been deposited in Genbank, accession number KU199806—incorporated herein by reference in its entirety, and described by Berekaa et al. [Int. J. Agr. Biol (2016) 18 (6) 1232-1236—incorporated herein by reference in its entirety]. SEQ ID NO: 1 was further analyzed by BLAST search (Genbank database of NCBI, NIH, USA) and submitted for acquisition of accession numbers. Phylogenetic analysis was carried out using ClustalW software and phylogenetic tree was generated using different Bacilli with their corresponding accession numbers: *Bacillus subtilis* strain DA7 (EU000054), *Bacillus cereus* strain SS263-34 (JX429824), *Bacillus thuringiensis* (EU159480), *Bacillus endophyticus* strain Cu33 (KX098462), *Bacillus endophyticus* strain 08BF03CD (KX146479), *Bacillus endophyticus* strain JUPR15 (KX010971) and *Bacillus megaterium* strain HTP02 (KX024729). Partial sequence of 16S rRNA of SEQ ID NO: 1, that comprises 445 nucleotides, displays 100% sequence homology to 16S rRNA of other *B. endophyticus* strains including *B. endophyticus* AVP9, *B. endophyticus* TMR1.22, and other *B. endophyticus* bacterial strains. FIG. 3 shows phylogenetic analysis of 16S rRNA with the corresponding nucleotide sequences from other related Bacilli (using BLAST-EXPLORER software) revealed the close similarity to other known *B. endophyticus* strains (Dereeper et al., 2010). Also, it showed very close relation to *B. subtilis*, rather than *B. megaterium*, *B. thuirngienses*, or *B. cereus* (FIG. 3).

The 16s ribosomal rDNA gene sequence has been deposited in GenBank under Accession number KU199806.1 and is described by SEQ ID NO: 1.

Example 2

(a) Production of Bioactive Compound

A seed culture of *B. endophyticus* DS43 was prepared by growing the bacterium in 50 mL of nutrient broth in 250 ml Erlenmeyer flask and incubated at 37° C. for 24 h in orbital shaker at 120 rpm. For detection of bioactive compound production 1.5% inoculums of overnight culture was used to inoculate three different media: nutrient broth medium (NB) with the following composition: 5 g/L peptone, 3 g/L beef extract, and 2 g/L NaCl; [modified LB medium (Bio World, US/Canada)]; and tryptone soy broth (TSB, pH 7.4) medium (OXOID, England).

The bacterium was cultivated in 50 mL of the medium in 250 mL Erlenmeyer flask and incubated at 37° C. for 48 h or 72 h in orbital shaker.

(b) Cultivation on Blood Agar

Figure 2A:
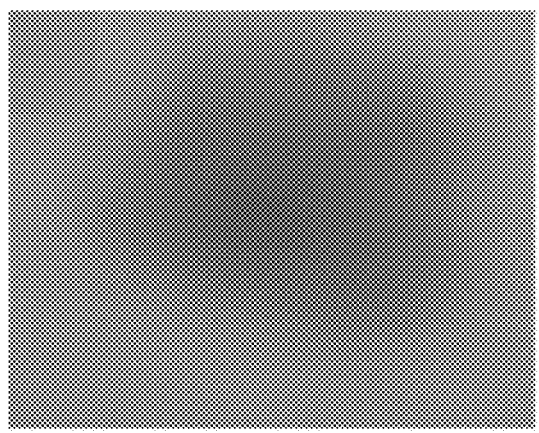
FIG. 2A shows the growth of *B. endophyticus* 43 on blood-agar medium under white light.
Figure 2B:
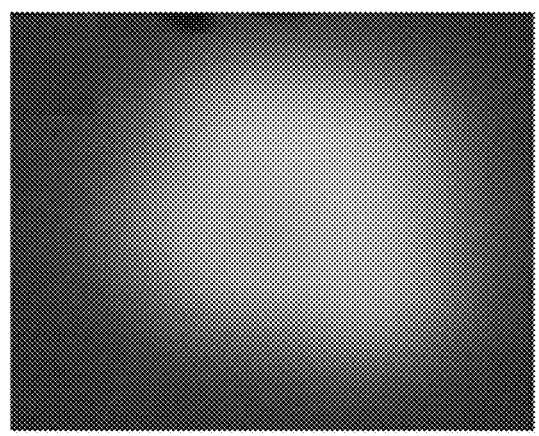
FIG. 2B shows the growth of *B. endophyticus* 43 on blood-agar medium under UV light.

To test hemolytic activity, the bioactive producing strain *B. endophyticus* DS43 producing strain was tested for hemolytic activity by cultivation on blood agar medium (Bioworld, USA). No haemolytic activity was observed (FIG. 2).

Example 3

Extraction of the Fluorescent Bioactive Compound

*B. endophyticus* DS43 was cultivated on tryptic soya agar (TSA) medium known to have 15 g enzymatic digest of casein, 5 g enzymatic digest of soyabean meal, and 15 g of NaCl for 48 to 72 hours under static condition. At the end of incubation period, the cells were removed from the surface of TSA plates by suspension in sterile distilled water, separated by centrifugation at 7500 rpm for 10 min, washed with distilled water, and re-centrifuged. The bioactive fluorescent compound was extracted by suspending cells in acetone and regular vortex every 10-15 min for 2 hours at room temperature. Finally, cell debris was separated by centrifugation at 10,000 rpm for 10 min, and the acetone supernatant containing the bioactive material was evaporated at room temperature. In some experiments, the acetone was replaced by methanol following the same procedure.

Example 4

Assay for Antibacterial Activity

*B. endophyticus* DS43 of NB, LB or TSB culture medium (10 mL) were centrifuged at 4000 rpm for 20 min to remove cells. The cell-free supernatant was sterilized by filtration using 0.45 µm Millipore bacterial filters and tested using the agar well diffusion assay against selected bacterial strains. Muller Hinton agar media plates swabbed with 75-100 µl of diluted and freshly grown indicator organism. For detection of the inhibitory effect, 200-300 µl of the sterilized supernatant was used to fill 11 mm diameter wells generated by Cork borer. Plates were incubated at 37° C. for 48 to 72 h. At the end of incubation period diameter of inhibition zone was determined. The bacterial candidates showed potential antimicrobial activity against many bacterial strains (Table 1). The cell extract showed yellow fluorescence under UV light (FIG. 1). Yellow light typically has a wavelength ranging from about 590 nm to 560 nm, green from about 560 to 520 nm, and cyan from about 520 to 490 nm, blue from about 490 to 450 nm and violet from about 450 to 400 nm.

TABLE 1

Screening of bioactive compound production by *Bacillus endophyticus* DS43 against different bacterial candidates

| | Size of inhibition zone (mm) | |
|---|---|---|
| Strain | Muller Hinton | Nutrient Agar medium |
| *Serratia marcescens* | +++ | ++ |
| *Klebsiella* sp | + | NA |
| *B. megaterium* DP7 | ++ | ++ |
| *B. anthracis* DWST2-3 | + | + |
| *P. aeruginosa* strain 209 | + | NA |
| *S. aureus* strain 12633 | ++ | + |
| *E. coli* | ++ | ++ |
| *Staphylococcus aureus* | +++ | ++ |

Figure 4A:
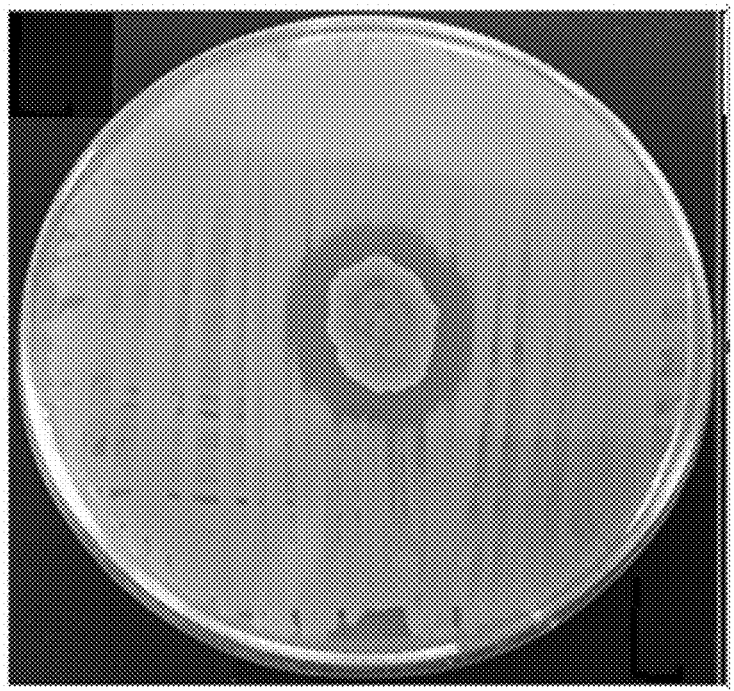
FIG. 4A shows the inhibitory effect of the bioactive preparation from *B. endophyticus* DS43 on *Serratia marcescens* during growth on TSA medium under white light.
Figure 4B:
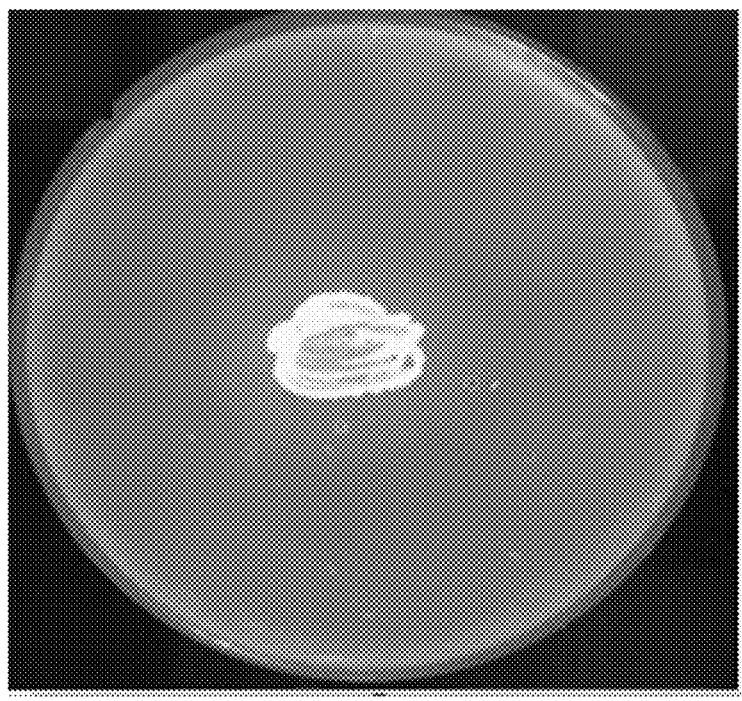
FIG. 4B shows the inhibitory effect of bioactive preparation from *B. endophyticus* DS43 on *Serratia marcescens* during growth on TSA medium under UV light.
Figure 5A:
FIG. 5A shows an extract of the bioactive compound from a culture of *B. endophyticus* DS43 with acetone or methanol under white light.
Figure 5B:
FIG. 5B shows an extract of the bioactive compound from a culture of *B. endophyticus* DS43 with acetone or methanol under ultra violet light.
Figure 5C:
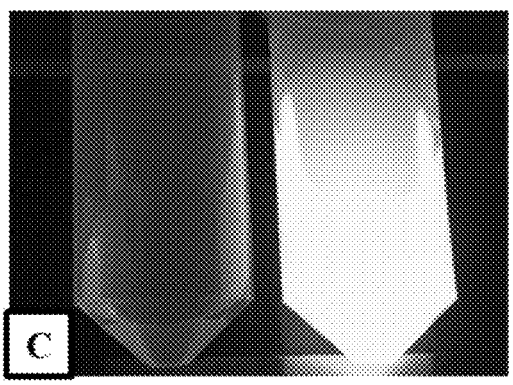
FIG. 5C shows an extract of the bioactive from *B. endophyticus* DS43 compound dissolved in acetone under ultra-violet light and a control.
Figure 5D:
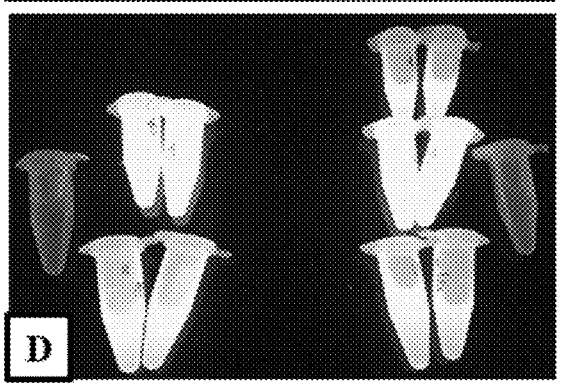
FIG. 5D shows an extract of the bioactive from *B. endophyticus* DS43 compound dissolved in methanol (right) and acetone (left) under ultra-violet light and a control.

Results in FIGS. 4a and 4b showed the inhibitory effect of *Bacillus endophyticus* DS43 on the indicator organism *Serratia marcescens* during growth on Muller Hinton medium at 37° C. for 72 h. The bioactive material can be extracted from cells grown on solid tryptic soya agar media after 48-72 hrs by acetone or methanol (FIG. 5) and display a characteristic absorption maximum at 518 nm in the UV/vis spectrum.

Example 5

Figure 6:
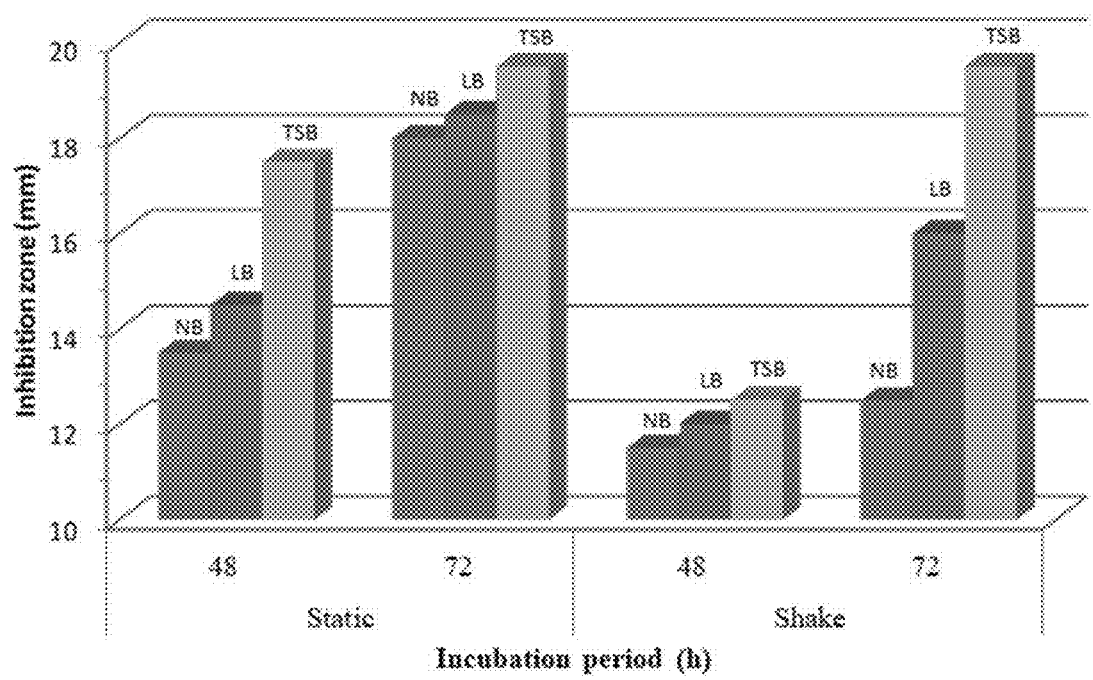
FIG. 6 illustrates the effect of media composition and incubation condition on the production of bioactive compound by *B. endophyticus* DS43 during different time intervals.

Culture medium from *Bacillus endophyticus* DS43 cultured in NB, LB, and TSB were obtained as described above. The bactericidal activity of each culture medium of *Bacillus endophyticus* DS43 was examined using cultures of *Serratia marcescens* as a model bacterium. FIG. 6 shows that the highest amount of bioactive compound produced by *Bacillus endophyticus* DS43 was observed after 72 h incubation period during growth on tryptone Soya Broth (TSB) medium, which shows 1.6-fold increase in activity in comparison with 48 h. Also, as compared to nutrient broth NB, Luria-Bertani LB, it display approximately 22% increase in bioactive compound production after 72 h cultivation period. The results collectively reflect the importance of cultivation medium composition and the cultivation condition on the bioactive compound production.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, these terms are synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim including additive or synergistic effects of combining a purine analog and a drug or agent that depletes ATP. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

As used herein, the term "and/or" includes any and all combinations of one or more of the associated listed items and may be abbreviated as "/".

Links are disabled by spelling out of or deletion of http: or by insertion of a space or underlined space before www. Unless otherwise indicated, the text available via the link on the filing date of the application is incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

Whenever a range is given in the specification, for example, a temperature range, a time range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method of producing a fluorescent composition, comprising:
   culturing Bacillus endophyticus or a bacillus having 16s rDNA that has 100% sequence identity with SEQ ID NO: 1 in a suitable medium containing phosphorous and date syrup,
   extracting the cultured bacillus with an organic solvent, and
   recovering a material from the organic solvent that is fluorescent under UV light;
   wherein the bacillus is Bacillus endophyticus DS43 which is described by accession number DSM 34706 at the DSMZ Patent Depository, Inhoffenstraße 7B, 38124 Braunschweig Science Campus Braunschweig-Süd GERMANY.

2. The method of claim 1, wherein the phosphorous in the suitable medium comprises disodium phosphate dodecahydrate at a concentration of ranging from 0.1 g/L-5 g/L.

3. The method of claim 1, wherein the date syrup comprises 25%-50% fructose, 30%-50% glucose, and 0.1%-20% sucrose, each relative to the total volume of the date syrup.

4. The method of claim 1, wherein the date syrup is in an amount of 0.5%-7% v/v relative to a total volume of the growth medium and the bacteria.

5. The method of claim 1, wherein the growth medium further comprises 0.1%-5% v/v molasses or palm sugar, relative to the total volume of the growth medium and bacteria.

6. The method of claim 1, wherein the suitable medium further comprises a tryptone soy broth (TSB) medium.

7. The method of claim 1, wherein the suitable medium further comprises nutrient broth or Luria-Bertani (LB) medium.

8. The method of claim 1, wherein the suitable medium further comprises a nutrient broth, 0.1 g/L-1 g/L of magnesium sulfate heptahydrate, and 1 mL/L-5 mL/L of a trace element solution, and the growth medium has a pH in the range of 3.0-10.0, wherein the trace element solution comprises 0.05 g/L-1 g/L of zinc sulfate heptahydrate, 0.01-1.0 g/L of manganese chloride tetrahydrate, and 0.01 g/L-1.0 g/L copper sulfate tetrahydrate.

9. The method of claim 1, wherein the suitable medium further comprises one or more of cysteine, leucine, methionine, tryptophan, histidine, glutamine and proline in an amount in the range of 0.05-0.5 wt. % of the total weight of the growth medium.

10. The method of claim 1, wherein the culturing comprises growing the bacilli at a growth temperature of 25° C.-40° C. under mechanical agitation in a fed-batch process vessel.

11. The method of claim 10, wherein the bacilli are cultured for 20-84 hours in a fed-batch phase where date syrup is administered to the bacilli.

12. The method of claim 11, wherein date syrup is administered in a pulse, a shot feeding, a linearly modulated feeding, an exponentially modulated feeding, or a constant feeding during the fed-batch phase.

13. The method of claim 1, wherein recovering the material from the organic solvent that is fluorescent under UV light comprises extracting it from an aqueous solution with an organic solvent and optionally further purifying it by chromatography.

14. The method of claim 1, wherein said fluorescent material exhibits a broad absorption peak at 518 nm.

15. A method of producing a fluorescent antibacterial composition comprising:
  culturing *Bacillus endophyticus* strain DS43 or a subculture thereof in tryptone soy broth (TSB) comprising date syrup for a time in the range of 24 h to 96 h at a temperature in the range of 25-48° C. to form the fluorescent antibacterial composition,
  separating Bacillus endophyticus from the culture medium, and
  isolating the one or more bioactive compounds from the separated *Bacillus endophyticus* wherein the fluorescent antibacterial composition exhibits bactericidal activity against *Serratia marcescens*.

* * * * *

SEQUENCE LISTING

<160> NUMBER OF SEQ ID NOS: 1

<210> SEQ ID NO 1
<211> LENGTH: 445
<212> TYPE: DNA
<213> ORGANISM: Bacillus endophyticus
<220> FEATURE:
<221> NAME/KEY: misc_feature
<222> LOCATION: (1)..(445)
<223> OTHER INFORMATION: Bacillus endophyticus strain DS43 16S ribosomal
      RNA gene, partial sequence
      GenBank: KU199806.1

<400> SEQUENCE: 1

| aatcttccgc | aatggacgaa | agtctgacgg | agcaacgccg | cgtgagtgat | gaaggttttc | 60 |
| ggatcgtaaa | gctctgttgt | tagggaagaa | caagtacctg | ttaaataagc | aggtaccttg | 120 |
| acggtaccta | accagaaagc | cacggctaac | tacgtgccaa | cagccgcggt | aatacgtagg | 180 |
| tggcaagcgt | tgtccggaat | tattgggcgt | aaagcgcgcg | caggcggttc | cttaagtctg | 240 |
| atgtgaaagc | ccacggctca | accgtggagg | gtcattggaa | actggggaac | ttgagtgcag | 300 |
| aagaggagag | cggaattcca | cgtgtagcgg | tgaaatgcgt | agagatgtgg | aggaacacca | 360 |
| gtggcgaagg | cggctctctg | gtctgtaact | gacgctgagg | cgcgaaagcg | tggggagcga | 420 |
| acaggattag | ataccctggt | agtcc | | | | 445 |